United States Patent
Feiweier et al.

(10) Patent No.: US 10,664,683 B2
(45) Date of Patent: May 26, 2020

(54) METHOD AND APPARATUS FOR CLASSIFYING MAGNETIC RESONANCE MEASUREMENT DATA ACQUIRED FROM AN EXAMINATION OBJECT USING A MAGNETIC RESONANCE FINGERPRINTING METHOD

(71) Applicant: Siemens Healthcare GmbH, Erlangen (DE)

(72) Inventors: Thorsten Feiweier, Poxdorf (DE); Stefan Huwer, Erlangen (DE); Mathias Nittka, Baiersdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 8 days.

(21) Appl. No.: 15/875,086

(22) Filed: Jan. 19, 2018

(65) Prior Publication Data
US 2018/0204045 A1    Jul. 19, 2018

(30) Foreign Application Priority Data

Jan. 19, 2017  (EP) .................... 17152234

(51) Int. Cl.
*G06K 9/00* (2006.01)
*A61B 5/055* (2006.01)
(Continued)

(52) U.S. Cl.
CPC .......... *G06K 9/00114* (2013.01); *A61B 5/055* (2013.01); *A61B 5/7267* (2013.01); *G01R 33/5608* (2013.01); *G06K 9/00087* (2013.01); *G16H 50/20* (2018.01); *A61B 2576/00* (2013.01); *G01R 33/24* (2013.01);
(Continued)

(58) Field of Classification Search
None
See application file for complete search history.

(56) References Cited

U.S. PATENT DOCUMENTS

| | | |
|---|---|---|
| 2013/0265047 A1 | 10/2013 | Griswold et al. |
| 2015/0285886 A1 | 10/2015 | Hwang |

(Continued)

FOREIGN PATENT DOCUMENTS

| | | |
|---|---|---|
| JP | 2015528384 A | 9/2015 |
| JP | 2016002464 A | 1/2016 |
| KR | 20160150091 A | 12/2016 |

OTHER PUBLICATIONS

Coppo, et al.: "Overview of Magnetic Resonance Fingerprinting"; MAGNETOM Flash; vol. 65, No. 2; pp. 12-21; (2016).
(Continued)

*Primary Examiner* — Douglas X Rodriguez
(74) *Attorney, Agent, or Firm* — Schiff Hardin LLP (57) ABSTRACT

In a method and computer and magnetic resonance (MR) apparatus for classifying MR measurement data acquired from an object under examination by execution of an MR fingerprinting method, wherein the MR measurement data include multiple MR signal profiles acquired by the MR fingerprinting method. At least one texture parameter is derived from the MR measurement data. The MR measurement data are classified into at least one tissue class using the at least one texture parameter. The classified MR measurement data are provided as an output.

10 Claims, 3 Drawing Sheets

(51) Int. Cl.
*G01R 33/56* (2006.01)
*A61B 5/00* (2006.01)
*G16H 50/20* (2018.01)
*G01R 33/48* (2006.01)
*G01R 33/24* (2006.01)
*G01R 33/50* (2006.01)
*G01R 33/561* (2006.01)

(52) U.S. Cl.
CPC .......... *G01R 33/4818* (2013.01); *G01R 33/50* (2013.01); *G01R 33/561* (2013.01)

(56) References Cited

U.S. PATENT DOCUMENTS

| | | |
|---|---|---|
| 2015/0301141 A1 | 10/2015 | Griswold et al. |
| 2015/0362578 A1 | 12/2015 | Biber et al. |
| 2015/0366484 A1 | 12/2015 | Grodzki |
| 2016/0033604 A1 | 2/2016 | Grodzki |
| 2016/0059041 A1 | 3/2016 | Grodzki et al. |
| 2016/0061922 A1 | 3/2016 | Grodzki et al. |
| 2016/0097830 A1 | 4/2016 | Grodzki et al. |
| 2016/0278661 A1* | 9/2016 | Griswold ............... A61B 5/055 |
| 2018/0313925 A1* | 11/2018 | Parker ................... A61B 5/055 |

OTHER PUBLICATIONS

Ma, et al.: "Magnetic resonance fingerprinting";: (Author Manuscript) Nature; vol. 495, Nr. 7440; pp. 187-192; (2013).

Badve et al.: "Quantitative differentiation of prostate cancer from normal peripheral zone using Magnetic Resonance Fingerprinting (MRF) and Diffusion Mapping"; Proc. Intl. Soc. Mag. Reson. Med.; vol. 23; p. 3848; (2015).

Larroza, et al.: "Texture Analysis in Magnetic Resonance Imaging: Review and Considerations for Future Applications"; Chapter 5 of Assessment of Cellular and Organ Function and Dysfunction using Direct and Derived MRI Methodologies; (2016).

KR Decision to Grant dated Jul. 8, 2019, Application No. 10-2018-0005576.

* cited by examiner

METHOD AND APPARATUS FOR CLASSIFYING MAGNETIC RESONANCE MEASUREMENT DATA ACQUIRED FROM AN EXAMINATION OBJECT USING A MAGNETIC RESONANCE FINGERPRINTING METHOD

BACKGROUND OF THE INVENTION

Field of the Invention

The present invention concerns a method for classifying magnetic resonance (MR) measurement data that have been acquired from an examination object by execution of a magnetic resonance fingerprinting method. The invention also concerns a classifying computer, a magnetic resonance apparatus, and a non-transitory, computer-readable data storage medium encoded with programming instructions, for implementing such a method.

Description of the Prior Art

In a magnetic resonance apparatus, also known as a magnetic resonance tomography system, the body to be examined of an object under examination, for example a patient, a healthy test subject, an animal or a phantom, is usually exposed by a basic field magnet to a high main basic magnetic field, for example of 1.5 or 3 or 7 Tesla. Gradient fields are activated by a gradient coil arrangement. Radio-frequency pulses, for example excitation pulses, are then emitted via a radio-frequency antenna by suitable antenna equipment, which results in the nuclear spins of specific atoms, resonantly excited by these radio-frequency pulses, being tilted by a defined flip angle relative to the magnetic field lines of the main magnetic field. Precession of the nuclear spins during their relaxation causes the emission of radio-frequency signals known as magnetic resonance signals, which are received by suitable radio-frequency antennas, and then further processed. The desired image data are reconstructed from the raw data acquired in this manner.

A specific magnetic resonance sequence, also known as a pulse sequence, composed of a succession of radio-frequency pulses, for example excitation pulses and refocusing pulses, together with gradient fields activated in a coordinated manner along different gradient axes in different spatial directions, must therefore be emitted for a particular measurement. Temporally matching read-out windows are set which specify the time intervals in which the induced magnetic resonance signals are acquired.

Interpreting the magnetic resonance measurement data acquired by such a magnetic resonance apparatus, in particular classifying tissue classes or locating disease processes, and differential diagnoses derived therefrom, typically requires expertise and considerable experience on the part of the reporting radiologist. Availability of magnetic resonance measurement data in a form that permits a direct conclusion as to tissue type to be drawn would be desirable.

Usually, magnetic resonance measurement data assume the form of weighted images. T1-weighted, T2-weighted or diffusion-weighted magnetic resonance measurement data may be generated, for example, using different measurement techniques. In this form of magnetic resonance measurement data, intensity values have no precisely specified correlation with T1 relaxation time, T2 relaxation time or diffusion. In particular, the intensity values may vary as a function of the measurement protocol used or model of magnetic resonance device. It is thus typically not feasible to derive tissue classes from the weighted images directly.

Quantitative magnetic resonance methods that can be used for capturing quantitative tissue parameter maps have been known for some time. For instance, quantitative T2 relaxation maps may be calculated from a number of measurements with different echo times (TE). T1 relaxation maps can be calculated from measurements with different flip angles. Measurements with different b values can yield ADC (apparent diffusion coefficient maps. Usually, separate measurements are made for each of the tissue parameter maps to be created. This can lead to long measurement times and entail a risk of spatial misregistration, for example in the event of patient movement.

One possible magnetic resonance fingerprinting method is known from Ma et al., "Magnetic Resonance Fingerprinting", Nature, 495, 187-192 (14 Mar. 2013). Various applications of the magnetic resonance fingerprinting method are known, for example, from patent applications. For example, determination of a spatially resolved distribution of a marker substance from US 2015/0366484 A1, movement correction of magnetic resonance fingerprinting measurement data from US 2016/0097830 A1, a temperature determination method from US 2016/0033604 A1, a method for determining the effects of radiotherapy from US 2016/0059041 A1 or a magnetic resonance fingerprinting method tailored for specific substances from US 2016/0061922 A1.

Magnetic resonance fingerprinting is a quantitative magnetic resonance method by means of which quantitative values for tissue parameters of an object under examination and thus tissue parameter maps can be determined. One advantage of magnetic resonance fingerprinting is that a number of tissue parameters, for example a T1 relaxation time and a T2 relaxation time can be simultaneously acquired in an individual measurement. In this manner, magnetic resonance fingerprinting can make it unnecessary to use a number of different capture sequences for acquiring multiple tissue parameters, and so reduce the complexity and/or acquisition time of a magnetic resonance examination.

Current multiparameter magnetic resonance measurement data are typically processed and interpreted pixel-by-pixel. An individual tissue, parameter map, for example a T1 relaxation map, a T2 relaxation map and an ADC map, can be generated for each tissue parameter. The various tissue parameter maps can then be visually interpreted side-by-side by a radiologist or in the form of an overlaid image ("fusion"). While the availability of the tissue parameter maps instead of weighted images does indeed facilitate the identification of tissue classes, interpretation of the tissue parameter values pixel-by-pixel nevertheless does require considerable experience. It has been found that each individual tissue parameter, taken alone, is typically not enough to allow a robust tissue classification to be carried out.

Alternatively, the multiparameter magnetic resonance measurement data can be correlated to one another voxel-by-voxel and processed accordingly. In this manner, it is possible to classify voxels that are located both in a specified T1 interval and in a specified T2 interval. Corresponding correlation maps can be calculated and displayed voxel-by-voxel. It has been found, however, that even voxel correlation maps are not enough to be able to classify magnetic resonance measurement data robustly into tissue classes.

SUMMARY OF THE INVENTION

An object of the invention is to enable an improved classification of magnetic resonance measurement data acquired from an object under examination, by using a magnetic resonance fingerprinting method.

The method according to the invention for classifying magnetic resonance measurement data, acquired from an object under examination, by using a magnetic resonance fingerprinting method, has the following method steps. Magnetic resonance (MR) measurement data of an object under examination are acquired, wherein the MR measurement data include a number of MR signal profiles acquired by an MR fingerprinting method. In a computer, at least one texture parameter is acquired from the MR measurement data. The MR measurement data are classified by the computer into at least one tissue class, using the at least one texture parameter. The classified MR measurement data are provided as an output from the computer.

Acquiring the magnetic resonance measurement data may involve acquiring the magnetic resonance measurement data by operation of a magnetic resonance apparatus (scanner), or loading previously acquired magnetic resonance measurement data from a database.

Acquiring the magnetic resonance measurement data by means of the magnetic resonance fingerprinting method in particular involves acquiring multiple magnetic resonance signal profiles of different voxels from an examination region of the object under examination. The multiple magnetic resonance signal profiles are then typically compared with a signal model. The multiple magnetic resonance signal profiles are typically acquired by a pseudorandomized or incoherent capture scheme. Alternatively, regular or coherent and/or completely scanned capture schemes for acquiring the multiple magnetic resonance signal profiles are also conceivable. It is in principle appropriate to measure the multiple magnetic resonance signal profiles in a non-equilibrium state. An acquired magnetic resonance signal profile from the multiple magnetic resonance signal profiles indicates how a signal value of a magnetic resonance signal captured in the particular voxel changes during acquisition of the magnetic resonance signal profile. The voxel here indicates the region from which the magnetic resonance signal profile is acquired.

In a typical application, the multiple magnetic resonance signal profiles are simultaneously acquired from a number of voxels. For this purpose, a number of raw images may be acquired in a temporal sequence by means of the magnetic resonance fingerprinting method, wherein the number of magnetic resonance signal profiles may then be formed over the individual voxels of the number of raw images. The magnetic resonance signal profiles are temporally resolved by a time interval of the capture of different magnetic resonance signals or the number of raw images.

The magnetic resonance fingerprinting method in particular involves setting different capture parameters for capturing the different magnetic resonance signals. The capture parameters may here be varied over the time interval of acquisition of the magnetic resonance signal profiles in a pseudorandomized or incoherent manner. Possible capture parameters that are modified during acquisition of the magnetic resonance signal profiles are, for example, an echo time, a repetition time, a configuration and/or number of radio-frequency pulses, a configuration and/or number of gradient pulses, a diffusion code etc. It is also conceivable for the non-equilibrium state during acquisition of the multiple signal profiles to be generated by suitable preparation modules, which may include a saturation pulse and/or an inversion pulse. In this manner, a magnetic resonance signal profile or "fingerprint," which is characteristic of the voxel, can be acquired by the magnetic resonance fingerprinting method.

The at least one texture parameter is derived from the magnetic resonance measurement data by a derivation algorithm. The magnetic resonance measurement data is thus introduced as input data into the derivation algorithm that has the at least one texture parameter as output data. The at least one texture parameter may be obtained directly from the magnetic resonance measurement data, in particular directly from the number of magnetic resonance signal profiles. It is also conceivable for the magnetic resonance measurement data to be introduced only indirectly into the derivation algorithm, i.e. for the magnetic resonance signal profiles to be initially further processed and for the product of the further processing of the magnetic resonance signal profiles then to be introduced into the derivation algorithm. Various options for how the magnetic resonance measurement data may be introduced into the derivation algorithm are described below.

A specific structure, in particular a tissue structure, image content or measurement data content may typically be described as a texture. In this manner, the at least one texture parameter can characterize the specific structure, in particular the tissue structure. The at least one texture parameter may serve to quantify spatial features in the magnetic resonance measurement data. The at least one texture parameter may include, for example, information about a spatial arrangement of measured intensities in the magnetic resonance measurement data Alternatively or additionally, the at least one texture parameter may also characterize temporal patterns in the magnetic resonance measurement data, for example how the magnetic resonance signals in the number of magnetic resonance signal profiles develop over time.

One or more texture parameters may be derived from the magnetic resonance measurement data. Various options for deriving texture parameters are known to those skilled in the art from the field of image processing. For example, the at least one texture parameter may be obtained by a statistical method and thus be a random texture parameter. Examples of such statistical texture parameters are: mean, variance, skewness, Markov random fields, co-occurrence matrices. It is also possible for the at least one texture parameter to be a structural texture parameter. The structural texture parameter may, for example, characterize an energy distribution, entropy, a contrast, or a homogeneity in the magnetic resonance measurement data. It is, of course, also conceivable to derive further texture parameters as may appear appropriate to those skilled in the art.

The magnetic resonance measurement data are classified by execution of a classification algorithm, which has the at least one texture parameter as input data and the classified magnetic resonance measurement data as output data. The magnetic resonance measurement data may be introduced, in addition to the at least one texture parameter, into the classification algorithm as input data in order to provide rough guidance in the classification of the at least one tissue class. Typically, however, the at least one texture parameter may be used instead of the magnetic resonance measurement data for classifying the magnetic resonance measurement data. The at least one texture parameter thus may amount to a new representation of the content of the magnetic resonance measurement data.

The magnetic resonance measurement data may be classified into one or more tissue classes. Classifying the magnetic resonance measurement data may involve directly classifying the magnetic resonance measurement data, i.e.

the multiple magnetic resonance signal profiles, or classifying the magnetic resonance image data reconstructed from the magnetic resonance measurement data. After classification, the at least one matching tissue class is assigned to different parts of the magnetic resonance measurement data or to the magnetic resonance image data reconstructed from the magnetic resonance measurement data. The classified magnetic resonance measurement data may accordingly include information as to the tissue class of the object under examination from which the specific parts of the magnetic resonance measurement data or the magnetic resonance image data reconstructed from the magnetic resonance measurement data have been acquired.

The at least one tissue class may characterize a tissue type or a tissue variety from which the magnetic resonance measurement data were acquired. The at least one tissue class may, for example, be adipose tissue, soft tissue, bone tissue, cartilaginous tissue, muscle tissue, etc. The at least one tissue class may also be tissue from a specific organ type, for example liver tissue, lung tissue, white matter, gray matter, etc. The at least one tissue class may also be air or background. It is also conceivable for the at least one tissue class to be a foreign body in the body of the object under examination, such as an implant material. In one important field of application, the at least one tissue class may involve tissue typing for the purpose of determining whether the tissue is normal or physiological tissue or conspicuous or pathological tissue. For instance, a classification into normal tissue and tumor tissue may be carried out. A classification into other pathological tissue varieties, such as scar tissue, may also be carried out. Further tissue classes as may appear appropriate to those skilled in the art, into which the magnetic resonance measurement data can be classified, are also conceivable.

Various methods may be used for classifying the magnetic resonance measurement data, in particular the feature vectors obtained during derivation of the at least one texture parameter. A k nearest neighbor method, a statistical Bayes classification, support vector machines, etc. may be used. Further classification methods as may appear appropriate to those skilled in the art are, of course, conceivable. In general, the quality to be achieved of the classifiers correlates with the suitability of the at least one texture parameter with regard to separability of different tissue classes.

In addition to the stated methods, it is also conceivable to use a self-learning method for classifying the magnetic resonance measurement data. Such a method usually involves directly learning the mapping of some of the magnetic resonance measurement data to a tissue class, using a sufficiently large random sample for training. Deep convolutional neural networks are one possible suitable representative of this type of classifiers. In this case, the texture parameter to be derived is no longer explicitly described, but is instead implicitly learned in the method for automatically classifying some of the magnetic resonance measurement data.

Providing the classified magnetic resonance measurement data may involve displaying the classified magnetic resonance measurement data on a display unit. The magnetic resonance measurement data may be displayed with its associated classification, for example in the form of segmentation and/or colored overlay. Providing the classified magnetic resonance measurement data may also involve saving the classified magnetic resonance measurement data in a database and/or passing on the classified magnetic resonance measurement data to a further processing unit for further processing. Providing, i.e. displaying and/or saving, the classified magnetic resonance measurement data may involve providing magnetic resonance image data reconstructed from the magnetic resonance measurement data in classified form.

The inventive procedure is based on the insight that a simple voxel-by-voxel assignment or classification of tissue classes into reconstructed magnetic resonance image data is frequently difficult because the tissue to be classified is typically spatially textured. Accordingly, diseased tissue may differ from healthy tissue by magnetic resonance measurement data or magnetic resonance image data reconstructed from magnetic resonance measurement data is spatially modified in a characteristic manner. Such characteristic variation may involve a locally bounded fluctuation ("speckled") or a gradual modification ("diffuse"). A radiologist's well-trained eye can recognize such structures, but a pixel-based classification is impractical.

The purpose of the proposed procedure is to make use of at least one texture parameter for improved classification of magnetic resonance measurement data acquired using a magnetic resonance fingerprinting method. In this manner, it is possible to make use of spatial and/or temporal features in the classification of the magnetic resonance measurement data. In this manner, the magnetic resonance fingerprinting method may be meaningfully extended so that it is no longer only the magnetic resonance signal profiles of the individual voxels that are considered separately from one another. Instead, the classification of magnetic resonance measurement data from the magnetic resonance fingerprinting method may be improved by considering spatial adjacency relationships of the magnetic resonance signal profiles.

The magnetic resonance fingerprinting method is particularly suitable for classifying magnetic resonance measurement data because the magnetic resonance fingerprinting method is inherently capable of establishing multiparameter quantitative tissue parameters. Since the magnetic resonance fingerprinting method is thus capable of yielding absolute or comparable measurement results over various measurements, the magnetic resonance measurement data obtained by the magnetic resonance fingerprinting method is particularly suitable for classification into the at least one tissue class.

It is precisely the use of the at least one texture parameter that permits the advantageous further development of the classification of the magnetic resonance measurement data obtained by use of the magnetic resonance fingerprinting method, because taking account of spatial and/or temporal structures in the magnetic resonance measurement data is capable of enabling more robust differentiation of tissue classes. In this manner, deviations from the norm can be located more effectively in comparison with a conventional purely voxel-based evaluation of the magnetic resonance measurement data obtained by means of the magnetic resonance fingerprinting method. The composition of tissue, for example in a tumor, is in fact usually too complex for it to be reliably assignable to a specific tissue type, let alone a disease, on the basis of the tissue parameters measured in an individual voxel, such as for example the T1 relaxation time and T2 relaxation time. For this reason, combining the quantitative magnetic resonance fingerprinting method with a consideration of the spatial and/or temporal features can be a considerable advantage for the classification of magnetic resonance measurement data.

In an embodiment, the magnetic resonance measurement data include a number of spatially resolved tissue parameter maps reconstructed from the multiple magnetic resonance signal profiles. The derivation of at least one texture parameter involves deriving a number of texture parameter maps from the number of spatially resolved tissue parameter maps. The magnetic resonance measurement data are classified using the number of texture parameter maps.

If the magnetic resonance measurement data are loaded from a database, spatially resolved tissue parameter maps, which have already been fully reconstructed, can be loaded from the database as part of the magnetic resonance measurement data. In this case, it is also conceivable for solely the spatially resolved tissue parameter maps, and not the multiple magnetic resonance signal profiles, to be loaded from the database.

If the magnetic resonance measurement data are acquired by operation of a magnetic resonance apparatus (scanner) as part of the method according to the invention, the spatially resolved tissue parameter maps are reconstructed, in particular voxel-by-voxel, from the magnetic resonance signal profiles. In such a magnetic resonance fingerprinting reconstruction, the number of magnetic resonance signal profiles are compared with a number of database signal profiles. The number of database signal profiles with which the number of magnetic resonance signal profiles are compared are stored in a database. A different database value for a number of tissue parameters is in each case assigned to the respective different database signal profiles. A specific database signal profile is then in each case the signal profile to be expected in the magnetic resonance fingerprinting method when a sample is examined, the material characteristics of which correspond to those of the associated database value of the number of tissue parameters. The database signal profiles may for example be established and/or simulated in a calibration measurement. The magnetic resonance fingerprinting method then typically provides that one database signal profile from the multiple of database signal profiles is assigned to the acquired magnetic resonance signal profile on the basis of the result of the signal comparison. The signal comparison may involve a determination of a similarity of the acquired magnetic resonance signal profile to the multiple database signal profiles, wherein the respective database signal profile from the multiple database signal profiles that is assigned to the voxel is that which has the greatest similarity to the magnetic resonance signal profile. The database values of the multiple tissue parameters which belong to the assigned database signal profile may then be set as a measured value for the plurality of tissue parameters. In this manner, the multiple spatially resolved tissue parameter maps may be present as the result of the magnetic resonance fingerprinting reconstruction, since the multiple magnetic resonance signal profiles are also acquired in a spatially resolved manner.

The multiple of tissue parameter maps can be a distribution of a number of tissue parameters. In this manner, the multiple tissue parameter maps may be viewed as multiparameter magnetic resonance measurement data. A selection of possible tissue parameters which can be quantified by the magnetic resonance fingerprinting method is: a T1 relaxation time, a T2 relaxation time, a diffusion value (for example an apparent diffusion coefficient (ADC)), a magnetization moment, a proton density, a resonant frequency, a concentration of a substance, etc. Further tissue parameters as may appear appropriate to those skilled in the art are also conceivable. The number of tissue parameter maps may quantify any desired combination of the stated tissue parameters. The magnetic resonance fingerprinting method typically establishes two, three or four tissue parameter maps that quantify two, three or four different tissue parameters. One advantage of the magnetic resonance fingerprinting method is that the number of tissue parameter maps can be measured simultaneously in an individual measurement. In this manner, the magnetic resonance fingerprinting method can make it unnecessary to use a number of different capture sequences for acquiring the multiple tissue parameter maps, and so reduce the complexity and/or capture time of a magnetic resonance examination.

At least one texture parameter map is determined from each acquired spatially resolved tissue parameter map. It is also conceivable for a number of texture parameter maps, which represent different texture characteristics, to be determined for each acquired spatially resolved tissue parameter map. It is also possible for texture parameter maps to be determined for only some of the spatially resolved tissue parameter maps. The texture parameter map represents a spatially resolved distribution of the texture parameter that is determined on the basis of the associated tissue parameter map.

It is furthermore conceivable for the texture parameter map to be produced for a combination of a number of tissue parameter maps. The entries from a number of tissue parameter maps may here be considered in combination when producing the texture parameter map. The number of tissue parameter maps may here be handled in a similar manner to different color channels of a color image, wherein the various tissue parameters are stored in different color channels.

In addition to the number of spatially resolved tissue parameter maps, a number of texture parameter maps are in particular obtained as a result. The number of texture parameter maps may now be used, instead of the number of spatially resolved tissue parameter maps, for classifying the magnetic resonance measurement data. It is also conceivable for still further information from the number of spatially resolved tissue parameter maps to be introduced into the classification of the magnetic resonance measurement data. In this manner, the number of tissue parameter maps are advantageously no longer, as in conventional methods, evaluated voxel-by-voxel in the classification of the magnetic resonance measurement data. Instead, spatial and/or temporal features may advantageously be used in the classification of the multiparameter magnetic resonance measurement data acquired by means of the magnetic resonance fingerprinting method.

In another embodiment, the derivation of the at least one texture parameter involves reconstructing at least one texture parameter map, wherein the plurality of magnetic resonance signal profiles are directly introduced into the reconstruction of the at least one texture parameter map, and the magnetic resonance measurement data are classified using the at least one texture parameter map.

Whereas in the preceding embodiment the multiple magnetic resonance signal profiles are introduced in particular only indirectly, via the reconstruction of the multiple tissue parameter maps, into the derivation of the at least one texture parameter, in this embodiment the at least one texture parameter is in particular directly derived from the multiple magnetic resonance signal profiles. For this purpose, the multiple magnetic resonance signal profiles are temporally and spatially analyzed in combination in order to extract the at least one texture parameter. There is thus no need to establish a number of tissue parameter maps, as is usual in conventional magnetic resonance fingerprinting.

Advantageously, the at least one texture parameter is directly derived from the multiple magnetic resonance signal profiles not solely on basis of the usual voxel-based comparison of magnetic resonance signal profiles with the database signal profiles. Instead, the magnetic resonance fingerprinting reconstruction is advantageously extended by also taking account of a spatial component that contains characteristic texture features.

In another embodiment, the magnetic resonance fingerprinting model used for reconstructing the at least one texture parameter map takes account of a spatial context of the plurality of magnetic resonance signal profiles. Local spatial structuring of the tissue of the object under examination may accordingly be taken into account right from the modeling of the temporal signal evolution of the multiple magnetic resonance signal profiles. Greater complexity of this magnetic resonance fingerprinting model can be reduced by suitable compression methods, for example a PCA (Principal Component Analysis). By taking account of the spatial context of the multiple magnetic resonance signal profiles, the at least one texture parameter map can be directly derived from those magnetic resonance fingerprinting signal profiles. Classification of the magnetic resonance measurement data on the basis of the at least one texture parameter map, in particular on the basis of a combination of various texture parameters, can accordingly be carried out in a straightforward manner.

In another embodiment, the at least one texture parameter is derived in a time-resolved manner over a time interval for acquisition of the multiple magnetic resonance signal profiles.

In this manner, more than one statistical texture parameter is determined via the magnetic resonance measurement data acquired over the entire time interval. The texture parameter varies over the time interval for acquisition of the multiple magnetic resonance signal profiles. The time interval for acquisition of the multiple magnetic resonance signal profiles is here defined by the start time and finish time for acquisition of the multiple magnetic resonance signal profiles. The at least one texture parameter may also only vary over only part of the time interval for acquisition of the multiple magnetic resonance signal profiles.

In a preferred embodiment, deriving the at least one time-resolved texture parameter involves reconstructing a number of time-resolved texture parameter maps over different temporal portions of the time interval for acquisition of the plurality of magnetic resonance signal profiles. The magnetic resonance measurement data may then be classified using the number of time-resolved texture parameter maps. For this purpose, a texture parameter map may be determined for each raw image acquired by the magnetic resonance fingerprinting method. Alternatively, a texture parameter map may be determined in each case for a sequence of a plurality of successive acquired raw images. A temporal sequence of different texture parameter maps is thus obtained as an intermediate result. Such maps may then be introduced into the classification of the magnetic resonance measurement data, with the temporal component providing additional information for the classification.

In another embodiment, the magnetic resonance measurement data from the at least one time-resolved texture parameter are classified using a database, wherein the database contains information about the temporal evolution of the at least one texture parameter over the time interval for acquisition of the multiple magnetic resonance signal profiles as a function of the at least one tissue class.

Instead of conventional magnetic resonance fingerprinting reconstruction, in which the magnetic resonance signal profiles are compared, in terms of amplitude and phase, with database signal profiles, the magnetic resonance fingerprinting reconstruction in accordance with the invention proceeds using the at least one time-resolved texture parameter. For this purpose, the time-resolved texture parameter is compared with database profiles of the time-resolved texture parameter that describe the temporal evolution of the at least one texture parameter over the time interval for acquisition of the multiple magnetic resonance signal profiles as a function of the at least one tissue class. The database stores a number of database profiles which describe the temporal evolution of the at least one texture parameter for a plurality of different tissue classes. The database profiles may be determined not only for different tissue types but also on the basis of tissue features or tissue characteristics (for example "normal" and "conspicuous" evolutions in texture).

The different tissue classes into which the magnetic resonance measurement data are to be classified are thus stored in relation to the number of database profiles. The database profile which best matches the measured temporal evolution of the at least one texture parameter can be established for the classification. A maximum of one internal product of the two vectors may, for example, be determined to this end. The tissue class assigned to the best matching database profile can then be selected as the classification result. In this manner, the desired classification may advantageously be directly available as the result of the reconstruction of the magnetic resonance fingerprinting measurement data.

In another embodiment, the magnetic resonance measurement data from the at least one time-resolved texture parameter are classified using at least one filter operation.

As an alternative to searching for the best match of the measured temporal evolution of the at least one texture parameter with the database profiles, the measured temporal evolution of the at least one texture parameter can be analyzed on the basis of a model or filter. At least one dedicated filter operation may here be used for extracting tissue characteristics for the classification into tissue classes from the measured temporal evolution of the at least one texture parameter. A Kalman filter operation is, for example, is suitable here. Nonlinear state models, for example with extended Kalman filter operations or with sequential Monte Carlo methods, may also be modeled. A further possibility for the filter operation is to use a self-learning filter, for example based on a neural network (also known as "deep learning"). In this case, training with training data records is appropriate. In this case, it is advantageously possible to dispense with designing a dedicated filter operation or a dedicated model.

In another embodiment, in the spatial domain used as the basis for deriving the at least one texture parameter, at least one length scale is determined on the basis of at least one of the following elements: an anatomical region from which the magnetic resonance measurement data have been acquired, a clinical problem underlying the acquisition of the magnetic resonance measurement data, a disease process expected in the object under examination, or image data previously acquired from the object under examination.

If a spatial texture parameter is to be derived from the magnetic resonance measurement data, it is advisable to provide a suitable definition of the length scale in the spatial domain which is used as the basis for deriving the at least one texture parameter. In this manner, the at least one texture parameter can be particularly suitably derived for classification of the magnetic resonance measurement data. Information about the object under examination or about the clinical problem may here serve as a suitable basis for defining the length scale. It is likewise conceivable to make use of information from an anatomical atlas for determining the length scale.

The length scale may be constant for the entire magnetic resonance examination. The length scale may also vary as a function of the position from which the magnetic resonance measurement data is acquired. Alternatively or additionally, in a hierarchical analysis, different length scales (for example from coarse to fine) can be used for deriving the at least one texture parameter, whereby further information for a robust classification into the at least one tissue class may be obtained.

The classifying computer according to the invention is configured to implement the method according to the invention.

The classifying computer according to the invention thus is configured to implement the method as described above for classifying magnetic resonance measurement data acquired from an object under examination using a magnetic resonance fingerprinting method. For this purpose, the classifying computer according to the invention has a measurement data acquisition unit for acquiring magnetic resonance measurement data from the object under examination, wherein the magnetic resonance measurement data contain a number of magnetic resonance signal profiles acquired by the execution of a magnetic resonance fingerprinting method. The classifying computer according to the invention furthermore has a derivation processor for deriving at least one texture parameter from the magnetic resonance measurement data. The classifying computer according to the invention furthermore has a classifier for classifying the magnetic resonance measurement data into at least one tissue class using the at least one texture parameter. The classifying computer according to the invention furthermore has an output interface for providing the classified magnetic resonance measurement data as an output.

The components of the classifying computer according to the invention may predominantly take the form of software components. In principle, however, these components may also in part, particularly when particularly rapid calculations are involved, be embodied in the form of software-assisted hardware components, for example FPGAs or the like. Likewise, the necessary interfaces, for example if it is only a matter of receiving data from other software components, may take the form of software interfaces. They may, however, also take the form of hardware interfaces which are driven by suitable software. It is, of course, also conceivable for a number of the stated components to be combined and embodied in the form of an individual software component or software-assisted hardware component A magnetic resonance apparatus according to the invention has a magnetic resonance data acquisition scanner and the classifying computer according to the invention.

The classifying computer may be configured to transmit control signals to the magnetic resonance scanner and/or to receive and/or process control signals in order to carry out the method according to the invention. The classifying computer may be integrated in the magnetic resonance apparatus. The classifying computer may also be installed separately from the magnetic resonance apparatus. The classifying computer may be connected to the magnetic resonance apparatus.

The aforementioned magnetic resonance measurement data are acquired by the scanner of the magnetic resonance apparatus. The magnetic resonance measurement data are then be transferred to the classifying computer for further processing. The classifying computer acquires the magnetic resonance measurement data via the aforementioned measurement data acquisition unit.

The present invention also encompasses a non-transitory, computer-readable data storage medium encoded with programming instructions that, when the storage medium is loaded into a computer, such as a computer associated with a magnetic resonance apparatus, cause the computer, or the magnetic resonance apparatus, to implement any or all embodiments of the method as described above.

The advantages of the classifying computer according to the invention and the magnetic resonance apparatus according to the invention, and the storage medium according to the invention substantially correspond to the advantages of the method according to the invention as described above in detail. Features, advantages and alternative embodiments mentioned in this context are likewise also applicable to the other aspects of the invention. The functional features of the method here take the form of corresponding physical modules, in particular hardware modules.

DESCRIPTION OF THE PREFERRED EMBODIMENTS

Figure 1:
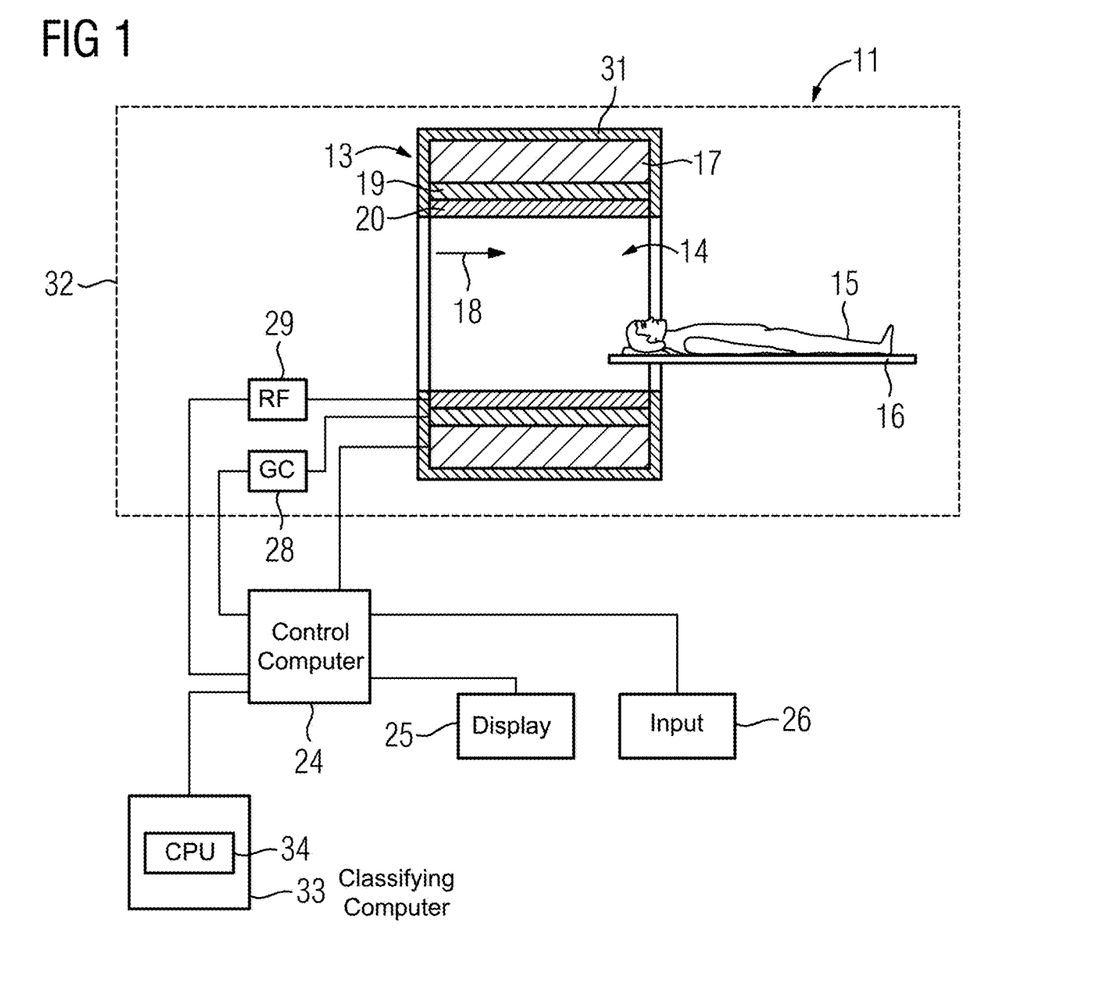
FIG. 1 schematically illustrates a magnetic resonance apparatus according to the invention with a classifying computer according to the invention.

FIG. 1 is a block diagram of a magnetic resonance apparatus 11 according to the invention with a classifying computer 33 according to the invention.

The magnetic resonance apparatus 11 has a magnetic resonance data acquisition scanner 13 with a basic field magnet 17 that generates a strong and constant basic magnetic field 18. The scanner 13 has a cylindrical patient accommodation zone 14 for accommodating an object under examination 15, in the present case a patient. The patient accommodation zone 14 is cylindrically enclosed at a circumference by the scanner 13. The patient 15 can be advanced into the patient accommodation zone 14 by a patient positioning apparatus 16. The patient positioning apparatus 16 has a patient table that is movable within the scanner 13. The scanner 13 is outwardly shielded by a housing enclosure 31.

The scanner 13 furthermore has a gradient coil arrangement 19 for generating magnetic field gradients that are used for spatially encoding the magnetic resonance signals. The gradient coil arrangement 19 is driven by a gradient controller 28. The scanner 13 further has a radio-frequency antenna 20, which in the case shown takes the form of a body coil fixedly integrated into the scanner 13 and a radio-frequency antenna controller 29 that operates the radio-frequency antenna 20 so as to emit radio-frequency magnetic resonance sequences into an examination chamber substantially formed by the patient accommodation zone 14. The radiated radio-frequency sequences excite certain nuclear spins so as to cause the magnetization thereof to deviate from the alignment produced by the basic magnetic field 18, by an amount known as a flip angle. As the excited nuclear spins relax, they emit the aforementioned magnetic resonance signals. The radio-frequency antenna 20 is furthermore designed to receive the magnetic resonance signals from the patient 15.

The magnetic resonance apparatus 11 has a control computer 24 that controls the basic field magnet 17, the gradient controller 28 and the radio-frequency antenna controller 29. The control computer 24 centrally controls the magnetic resonance apparatus 11, such as for the performance of a predetermined imaging gradient echo sequence. Control information such as imaging parameters, as well as reconstructed magnetic resonance images can be provided for a user on a display monitor 25 of the magnetic resonance apparatus 11. The magnetic resonance apparatus 11 furthermore has an input unit 26, via which information and/or parameters may be entered by a user during a measurement procedure. The control computer 24 may include the gradient controller 28 and/or the radio-frequency antenna controller 29 and/or the display monitor 25 and/or the input unit 26.

The magnetic resonance apparatus 11 furthermore comprises an acquisition unit 32. In the present case, the acquisition unit 32 is formed by the computer 13 together with the radio-frequency antenna controller 29 and the gradient controller 28.

The illustrated magnetic resonance apparatus 11 may have further components that magnetic resonance apparatuses usually have. The general manner of operation of a magnetic resonance apparatus is known to those skilled in the art, and therefore a more detailed explanation is not necessary herein.

The illustrated classifying computer 33 has a computing processor 34. This computing processor 34 may have various components, such as a measurement data acquisition unit, a derivation unit, a classifier or a provision unit, in order to carry out the method according to the invention.

The magnetic resonance apparatus 11 is thus designed, together with the classifying computer 33, to carry out the method according to the invention. The computing processor 34 of the classifying computer 33 acquires the magnetic resonance measurement data from the control computer 24 of the magnetic resonance apparatus 11. For this purpose, the computing processor 34 is connected for data exchange to the control computer 24 of the magnetic resonance apparatus 11. The classified magnetic resonance measurement data may then be transferred from the computing processor 34 to the display monitor 25 of the magnetic resonance apparatus 11 for display.

As an alternative to the illustration, the classifying computer 33 may be designed to carry out the method according to the invention by itself. To this end, the computing processor 34 will typically load the magnetic resonance measurement data from a database and/or retrieve it from the magnetic resonance apparatus 11.

Figure 2:
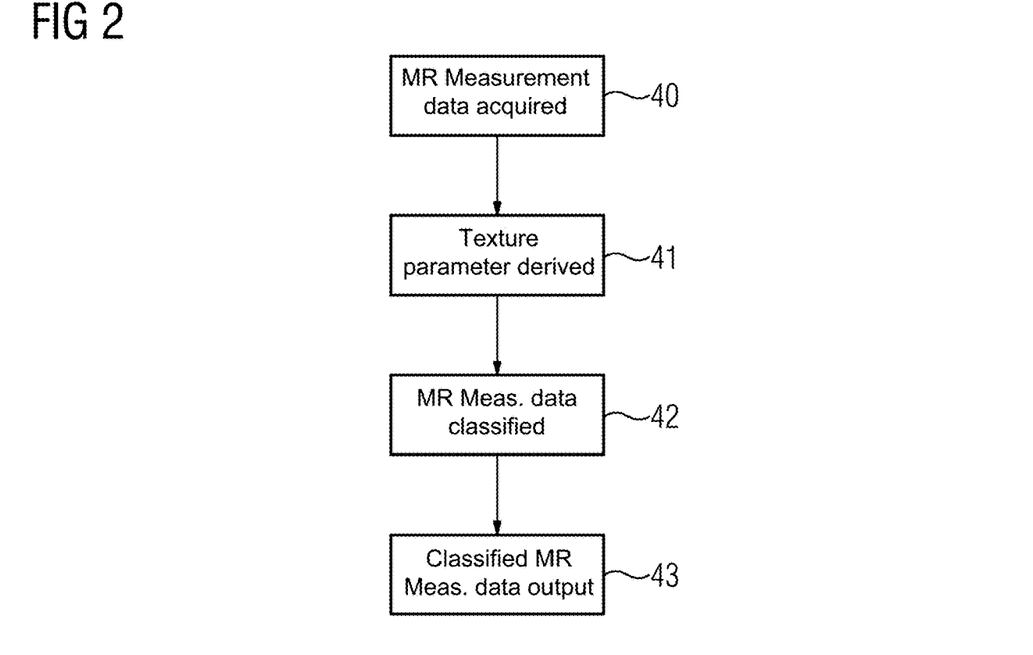
FIG. 2 is a flowchart of a first embodiment of the method according to the invention.

FIG. 2 shows a flowchart of a first embodiment of the method according to the invention for classifying magnetic resonance measurement data acquired from an object under examination 15 using a magnetic resonance fingerprinting method.

In a first method step 40, magnetic resonance measurement data are acquired from the object under examination, wherein the magnetic resonance measurement data include multiple magnetic resonance signal profiles acquired by execution of a magnetic resonance fingerprinting method.

In a further method step 41, at least one texture parameter is derived from the magnetic resonance measurement data.

In a further method step 42, the magnetic resonance measurement data are classified into at least one tissue class using the at least one texture parameter.

In a further method step 43, the classified magnetic resonance measurement data are provided as an electronic output (data file).

The following description is substantially limited to the differences relative to the exemplary embodiment in FIG. 2, wherein, with regard to method steps which remain the same, reference is made to the description of the exemplary embodiment in FIG. 2. Method steps that remain substantially the same are in principle provided with the same reference signs.

Figure 3:
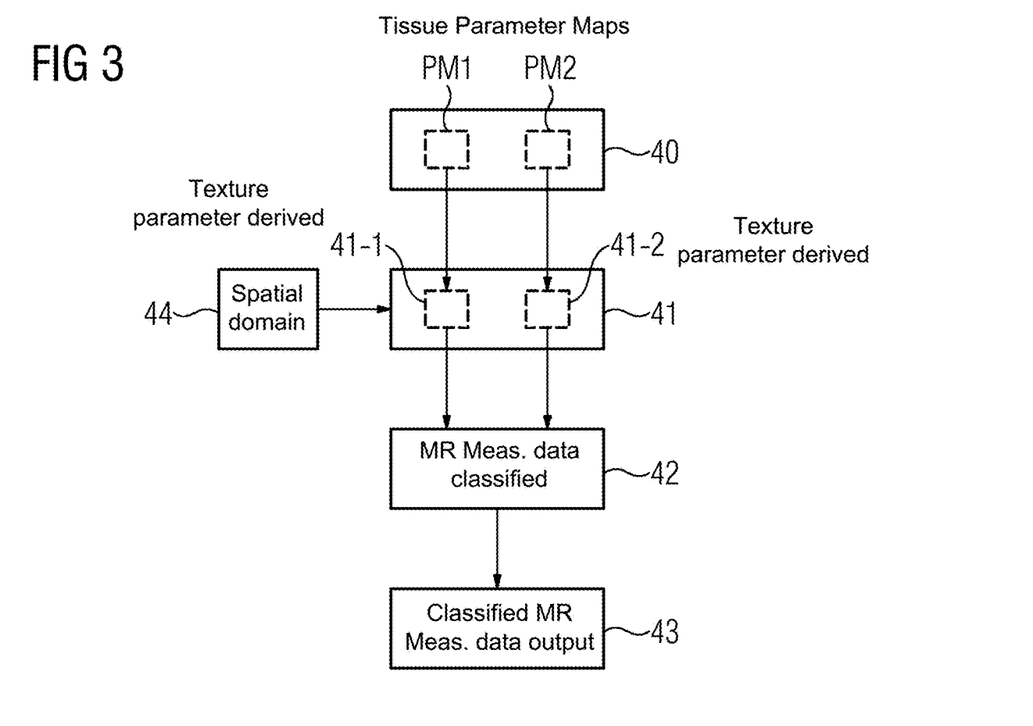
FIG. 3 is a flowchart of a second embodiment of the method according to the invention.
Figure 4:
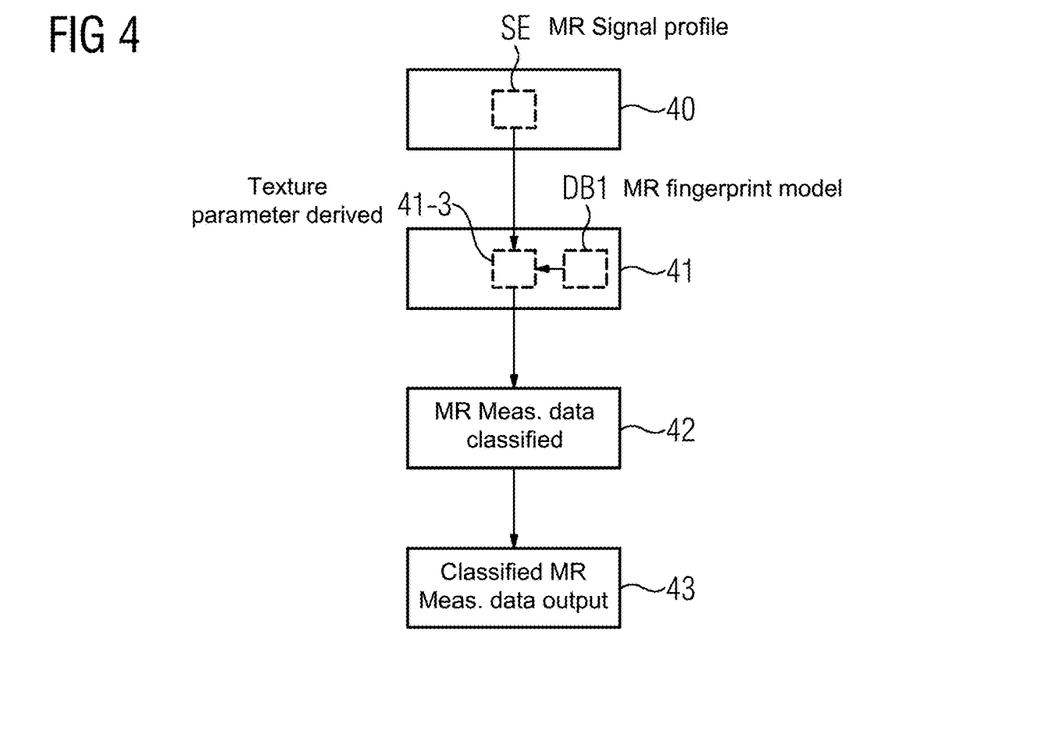
FIG. 4 is a flowchart of a third embodiment of the method according to the invention.
Figure 5:
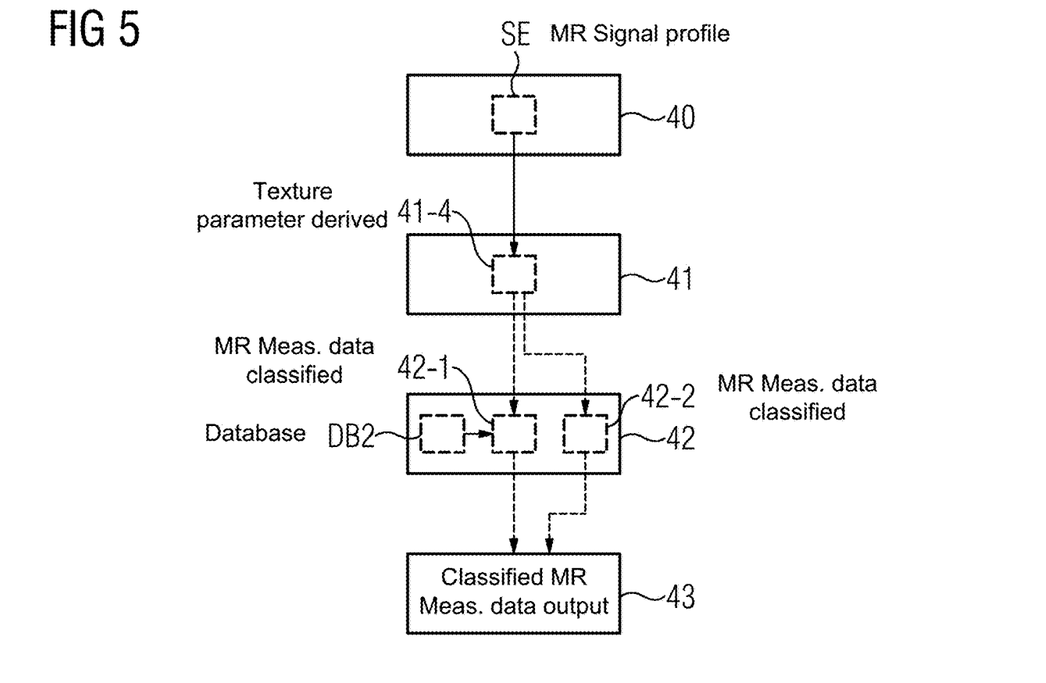
FIG. 5 is a flowchart of a fourth embodiment of the method according to the invention.

The embodiments of the method according to the invention shown in FIG. 3-FIG. 5 include method steps 40, 41, 42, 43 of the first embodiment of the method according to the invention according to FIG. 2. In addition, the embodiments of the method according to the invention shown in FIG. 3-FIG. 5 comprise additional method steps and substeps. An alternative method sequence to FIG. 3-FIG. 5 that have only some of the additional method steps and/or substeps shown in FIG. 3-FIG. 5 is also conceivable. An alternative method sequence to FIG. 3-FIG. 5 may have additional method steps and/or substeps.

FIG. 3 shows a flowchart of a second embodiment of the method according to the invention for classifying magnetic resonance measurement data acquired from an object under examination 15 by execution of a magnetic resonance fingerprinting method.

In the case shown in FIG. 3, the magnetic resonance measurement data include a number of spatially resolved tissue parameter maps PM1, PM2 reconstructed from the multiple magnetic resonance signal profiles. A first tissue parameter map PM1 and a second tissue parameter map PM2 are shown as examples. The magnetic resonance measurement data may also include more tissue parameter maps PM1, PM2. The first tissue parameter map PM1 and the second tissue parameter map PM2 here quantify different tissue parameters. For example, the first tissue parameter map PM1 may be a spatially resolved distribution of a T1 relaxation time and the second tissue parameter map PM2 may be a spatially resolved distribution of a T2 relaxation time. Other combinations of tissue parameters quantified in the tissue parameter maps are conceivable.

In the further method step 41, deriving the at least one texture parameter now involves deriving a number of texture parameter maps from the plurality of spatially resolved tissue parameter maps in two substeps 41-1 and 41-2. In the case shown in FIG. 3, a first texture parameter map is here derived from the first tissue parameter map PM1 in a first substep 41-1 of the further method step 41. In the case shown in FIG. 3, a second texture parameter map is here derived from the second tissue parameter map PM1 in a second substep 41-2 of the further method step 41. The two texture parameter maps may thus contain information about spatial and/or temporal structures in the respective associated tissue parameter map PM1 or PM2. More texture parameter maps may also be derived from the tissue parameter maps PM1 and PM2. For example, two or more than two different texture parameter maps which characterize different patterns in the first tissue parameter map PM1 may accordingly be determined in relation to the first tissue parameter map PM1 in the first substep 41-1. The second tissue parameter map PM2 may then be analyzed in a similar manner to the first tissue parameter map PM1.

The magnetic resonance measurement data are then classified in the further method step 42 using the plurality of texture parameter maps, in the case shown in FIG. 3 using the first texture parameter map and the second texture parameter map.

FIG. 3 shows a further method step 44, in which, in the spatial domain used as the basis for deriving the at least one texture parameter, at least one length scale is determined on the basis of at least one of the following elements: an anatomical region from which the magnetic resonance measurement data has been acquired, a clinical problem underlying the acquisition of the magnetic resonance measurement data, a disease process expected in the object under examination or image data previously acquired from the object under examination. Alternatively, this further method step 44 may also be carried out in the embodiments described in FIG. 4 or FIG. 5.

FIG. 4 shows a flowchart of a third embodiment of the method according to the invention for classifying magnetic resonance measurement data acquired from an object under examination 15 by execution of a magnetic resonance fingerprinting method.

In the case shown in FIG. 4, the number of magnetic resonance signal profiles SE acquired in the further method step 40 are directly further processed in the further method step 41.

For this purpose, deriving the at least one texture parameter in the further method step 41 involves reconstructing at least one texture parameter map in a substep 41-3 of the further method step 41, wherein the number of magnetic resonance signal profiles SE are directly introduced into the reconstruction of the at least one texture parameter map. The magnetic resonance fingerprinting model DB1 used in substep 41-3 for reconstructing the least one texture parameter map may here take account of a spatial context of the plurality of magnetic resonance signal profiles.

The magnetic resonance measurement data are then classified in the further method step 42 using the at least one texture parameter map.

FIG. 5 shows a flowchart of a fourth embodiment of the method according to the invention for classifying magnetic resonance measurement data acquired from an object under examination 15 by execution of a magnetic resonance fingerprinting method.

In the case shown in FIG. 5, the at least one texture parameter is derived in a substep 41-4 of the further method step 41 in a time-resolved manner over a time interval for acquisition of the number of magnetic resonance signal profiles SE.

The magnetic resonance measurement data may then be classified in the further method step 42 by either of two alternatives.

According to the first alternative, the magnetic resonance measurement data from the at least one time-resolved texture parameter are classified using a database DB2 in a first substep 42-1 of the further method step 42, wherein the database DB2 contains information about a temporal evolution of the at least one texture parameter over the time interval for acquisition of the plurality of magnetic resonance signal profiles SE as a function of the at least one tissue class.

According to the second alternative, the magnetic resonance measurement data from the at least one time-resolved texture parameter are classified using at least one filter operation in a second substep 42-2 of the further method step 42. The filter operation may also be used in the other embodiments according to FIG. 3 or FIG. 4 as an alternative to the direct comparison of the modeled magnetic resonance signal profiles with the database signal profiles.

The method steps shown in FIGS. 2-5 of the method according to the invention are carried out by the computing processor 34. To this end, the computing processor 34 has software and/or computer programs, which are stored in a memory of the computing processor 34. The software and/or computer programs include program code designed to carry out the method according to the invention when executed in the computing processor 34.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for classifying magnetic resonance (MR) measurement data acquired from an object by execution of an MR fingerprinting method, said method for classifying comprising:

with a computer, controlling an MR data acquisition scanner to execute an MR fingerprint method to acquire MR measurement data of an object, said MR measurement data comprising a plurality of MR signal profiles acquired by execution of said MR fingerprinting method and a plurality of spatially resolved tissue parameter maps reconstructed from said plurality of MR signal profiles;

in said computer, deriving a plurality of texture parameter maps from the plurality of spatially resolved tissue parameter maps to derive at least one texture parameter from said MR measurement data;

in said computer, classifying the MR measurement data into at least one tissue class using said at least one texture parameter and the plurality of texture parameter maps; and in said computer, generating an electronic signal corresponding to the classified MR measurement data and providing the electronic signal as an output from said computer.

2. A method as claimed in claim 1 comprising, in said computer:

deriving said at least one texture parameter by implementing a reconstruction algorithm in order to reconstruct at least one texture parameter map of the plurality of texture parameter maps, with said plurality of MR signal profiles being directly introduced into said reconstruction algorithm; and classifying said MR measurement data using said at least one texture parameter map.

3. A method as claimed in claim 2 comprising, in said reconstruction algorithm, using an MR fingerprinting model in which a spatial context of said plurality of MR signal profiles is modeled.

4. A method as claimed in claim 1 comprising, in said computer, deriving said at least one texture parameter with a time-resolution over a time interval during which said plurality of MR signal profiles were acquired.

5. A method as claimed in claim 4 comprising classifying said MR measurement data from said at least one time-resolved texture parameter using a database comprising information representing a temporal evolution of said at least one texture parameter over said time interval, as a function of at least one tissue class.

6. A method as claimed in claim 4 comprising using at least one filter operation to classify said MR measurement data from said at least one time-resolved texture parameter.

7. A method as claimed in claim 1 comprising deriving said at least one texture parameter in the spatial domain in which a length scale is determined based on at least one element selected from the group consisting of an anatomical region from which said MR measurement data were acquired, a clinical problem underlying the acquisition of said MR measurement data, a disease process that is suspected in said examination object, an image data previously acquired from said examination object.

8. A classifying computer comprising:
a processor configured to control an MR data acquisition scanner to execute an MR fingerprint method to acquire MR measurement data of an object;
an input interface configured to receive said MR measurement data of said object from said MR data acquisition scanner and into said processor, said MR measurement data comprising a plurality of MR signal profiles acquired by execution of said MR fingerprinting method and a plurality of spatially resolved tissue parameter maps reconstructed from said plurality of MR signal profiles;
said processor being configured to derive a plurality of texture parameter maps from the plurality of spatially resolved tissue parameter maps to derive at least one texture parameter from said MR measurement data;
said processor being configured to classify the MR measurement data into at least one tissue class using said at least one texture parameter and the plurality of texture parameter maps; and
an output interface at which said processor is configured to provide the classified MR measurement data in electronic form as an output from said processor.

9. A magnetic resonance (MR) apparatus comprising:
an MR data acquisition scanner;
a control computer configured to control the MR data acquisition scanner to execute an MR fingerprinting method to acquire MR measurement data from an examination object, so that the MR measurement data comprises a plurality of MR signal profiles acquired with said MR fingerprinting method and a plurality of spatially resolved tissue parameter maps reconstructed from said plurality of MR signal profiles;
said control computer being configured to derive a plurality of texture parameter maps from the plurality of spatially resolved tissue parameter maps to derive at least one texture parameter from said MR measurement data;
said control computer being configured to classify the MR measurement data into at least one tissue class using said at least one texture parameter and the plurality of texture parameter maps; and
said control computer being configured to provide the classified MR measurement data in electronic form as an output from said computer.

10. A non-transitory, computer-readable data storage medium encoded with programming instructions, said storage medium being loaded into a computer and said programming instructions causing said computer to:
control an MR data acquisition scanner to execute an MR fingerprint method to acquire MR measurement data of an object;
receive said MR measurement data of said object, said MR measurement data comprising a plurality of MR signal profiles acquired by execution of said MR fingerprinting method and a plurality of spatially resolved tissue parameter maps reconstructed from said plurality of MR signal profiles;
derive a plurality of texture parameter maps from the plurality of spatially resolved tissue parameter maps to derive at least one texture parameter from said MR measurement data;
classify the MR measurement data into at least one tissue class using said at least one texture parameter and the plurality of texture parameter maps; and
provide the classified MR measurement data in electronic form as an output from said computer.

* * * * *